United States Patent
Paul

(10) Patent No.: US 6,378,329 B1
(45) Date of Patent: Apr. 30, 2002

(54) METHOD FOR DETERMINING THE VARIABLE CONCENTRATIONS OF ICE IN BINARY ICE VOLUMES

(75) Inventor: Joachim Paul, Flensburg (DE)

(73) Assignee: Integral Energietechnik GmbH, Flensburg (DE)

( * ) Notice: Subject to any disclaimer, the term of this patent is extended or adjusted under 35 U.S.C. 154(b) by 0 days.

(21) Appl. No.: 09/762,009

(22) PCT Filed: Jul. 22, 1999

(86) PCT No.: PCT/DE99/02307

§ 371 Date: Jan. 31, 2001

§ 102(e) Date: Jan. 31, 2001

(87) PCT Pub. No.: WO00/08436

PCT Pub. Date: Feb. 17, 2000

(30) Foreign Application Priority Data

Aug. 1, 1998 (DE) .......................................... 198 34 781

(51) Int. Cl.$^7$ ................................................. B01D 9/04
(52) U.S. Cl. ........................................... 62/544; 62/136
(58) Field of Search .......................... 62/136, 342, 354, 62/544

(56) References Cited

U.S. PATENT DOCUMENTS

| 3,328,972 | A | * | 7/1967 | Svanoe | 62/544 |
| 3,407,618 | A | * | 10/1968 | Mullins, Jr. | 62/136 |
| 3,410,103 | A | * | 11/1968 | Cornelius | 62/136 |
| 4,275,567 | A | * | 6/1981 | Schwitters | 62/136 |
| 4,551,159 | A | * | 11/1985 | Goldstein | 62/544 |
| 4,653,313 | A | | 3/1987 | Sabins et al. | |
| 4,888,976 | A | | 12/1989 | Vermeiren | |
| 6,301,904 | B1 | * | 10/2001 | Goldstein | 62/136 |

FOREIGN PATENT DOCUMENTS

| DE | 43 25 794 C1 | 10/1994 |
| JP | 61066143 | 4/1986 |
| WO | WO 97/48973 | 12/1997 |

\* cited by examiner

*Primary Examiner*—William E. Tapolcai
(74) *Attorney, Agent, or Firm*—Larson & Larson, P.A.; James E. Larson

(57) ABSTRACT

Method for determining changing ice concentration in binary ice volumes with the steps: carrying out mechanical work in the volume to be measured with an electric motor, determining the electric power and mathematical conversion into a measure for the ice concentration.

7 Claims, 2 Drawing Sheets

METHOD FOR DETERMINING THE VARIABLE CONCENTRATIONS OF ICE IN BINARY ICE VOLUMES

PRIOR APPLICATIONS

Figure 1:
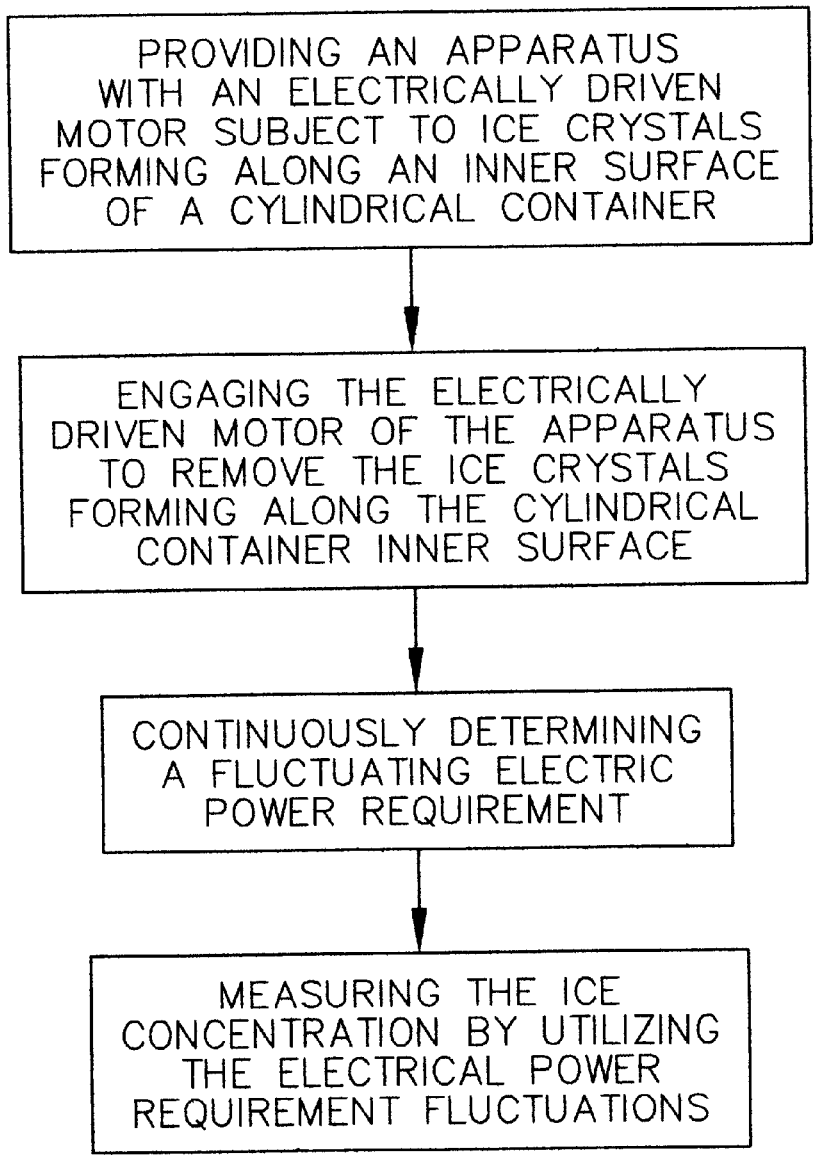

This application is a §371 U.S. National Phase application which bases priority on International Application No. PCT/DE 99/02307, filed Jul. 22, 1999, which in turn bases priority on German Application No. DE 198 34 781.2, filed Aug. 1, 1998.

BACKGROUND OF THE INVENTION

1. Field of the Invention

The invention relates to a method for determining varying ice concentrations in binary ice volumes. Binary ice, i.e. a suspension of small ice crystals in an aqueous solution or mixture, is used in widely varying forms for refrigerated transportation, refrigerated storage and refrigerated use.

2. Description of the Prior Art

Unlike in the case of other, single-phase liquid coolants (e.g. water, brine, etc.) there is no or only an insignificant binary ice temperature change for as long as ice crystals are present in this two-phase fluid. Heat supply does not lead to a significant temperature rise and instead the ice crystals melt (latent energy).

To be able to control the use of binary ice, it is necessary to determine the ice concentration in the binary ice volume. This has hitherto been carried out inter alia by the measurement of the electrical conductivity or electrical conduction resistance, as well as the measurement of the pressure in a closed storage container and in each case only an indirect conclusion concerning the ice concentration is possible, which is in particular inadequate if the external framework conditions do not remain constant.

Thus, e.g. in systems where the chemical composition of the binary ice fluid is not constant, the electrical conductivity cannot be a reliable measure for the ice concentration. The same applies for non-closed systems with a non-constant mass, in which volume changes would be expressed as an ice concentration change, which leads to errors. The measurement of the density of the binary ice fluid is very complicated and must be eliminated for cost reasons, particularly in smaller plants. A determination of the viscosity of the binary ice fluid as a measure for the ice concentration is impossible with conventional methods, because binary ice is a non-Newtonian fluid (it is a Bingham fluid) and consequently does not supply a usable signal for the ice concentration.

Calorimetric determinations of the ice concentration are only suitable on a laboratory scale, because they require manual measures.

For a discussion of the state of the art, U.S. Pat. No. 4,888,976 is named, wherein an apparatus for recording the viscosity of a lubricant is described in which components to be provided additionally with at least two parts are proposed, and which are positioned movable in relation to each other and which are driven by a motor. Also WO 97/48973 is known, wherein an impeller rotates in a fluid for measurement of the consistency of a paper pulp or the like. In both references a multitude of additional parts are needed, which makes the measurement technological large scale and the cost of repair expensive.

The problem of the invention is therefore to provide a method with which it is possible to determine the ice concentration in binary ice volumes.

SUMMARY OF THE INVENTION

According to the invention this problem is solved by a method having the features of the main claim. The subclaims provide advantageous embodiments of the invention.

Particularly as a result of carrying out mechanical work in the volume to be measured with an electric motor, particularly if the motor drives a scraper configuration, a mathematical conversion is possible, which enables conclusions to be drawn regarding the ice concentration from the electric power determined.

However, it is also conceivable to use a stirrer in an ice accumulator, optionally in addition to the scraper configuration, for a more precise mathematical conversion. It is also possible to use the electric power of a binary ice fluid-delivering pump for determining the ice concentration.

It is additionally possible to measure the pump pressure, which is produced on conveying binary ice in a pipeline. This pressure is not related to the binary ice pressure through expansion with increasing ice concentration.

Further advantages and features of the invention can be gathered from the following description of a preferred embodiment of the method.

DETAILED DESCRIPTION OF THE PREFERRED EMBODIMENT

1. Mechanical Method

In the method of the present invention, clearly defined signals varying with an ice concentration are produced allowing a determination of said ice concentration, particularly on again calibrating the same to the expected chemical compositions of a binary ice fluid.

Figure 2:
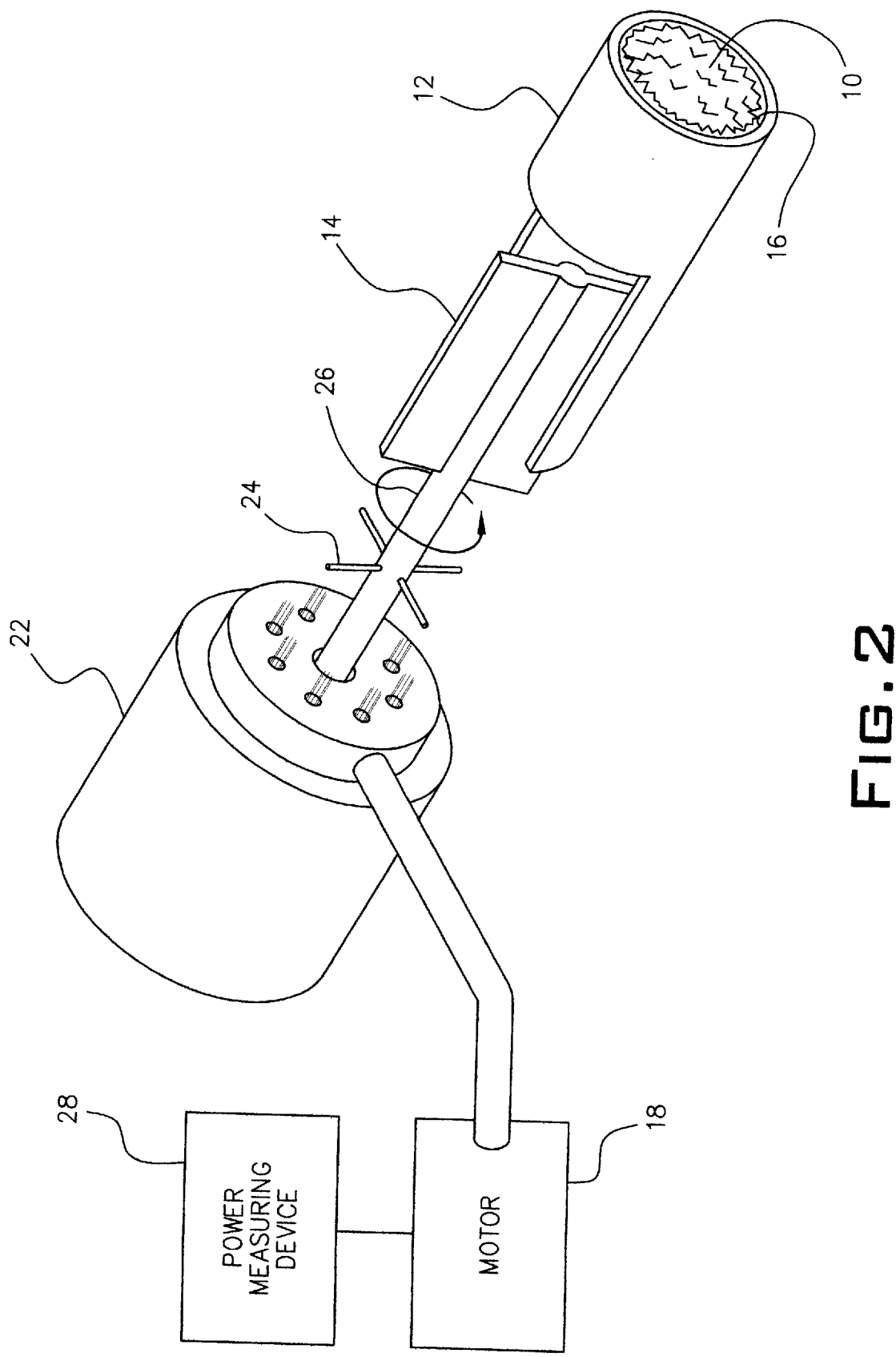

As shown FIG. 2, ice crystals 10 are produced in a cylindrical container 12 through which the binary ice fluid flows. The cylindrical container 12 is cooled from the outside with an evaporating refrigerant or a liquid coolant. Thus, ice crystals 10 form on a surface of an inside 16 of the cylindrical container 12 and are removed by a suitably constructed scraper 14 configuration.

With continuing reference to FIG. 2, it is shown that the necessary drive power of the scraper 14 configuration is e.g. a function of the contact pressure of the scraper 14 on the surface of the inside 16 of the cylinder 12, the length of the cylinder, the number of scrapers, the coefficients of friction of the material pair surface/scraper, hydraulic quantities (flow), pressure drop, fluid temperature, etc., the accuracy to size of the cylinder 12 and the scraper 14, the refrigerating capacity, the speed of the scraper 14 configuration (rotational speed) and the thickness of the ice crystals 10 or the ice coating. Whilst taking account of the particular parameters during the mathematical conversion it is then possible to draw conclusions from the electrical active power requirement on the increasing ice concentration of the fluid.

As shown in FIG. 2, the scraper 14 is driven by means of a motor 18 ensuring the rotary movement of the scraper 14 configuration. Apart from the aforementioned systematic powers, the ice concentration is codeterminative for the necessary motor power. It is therefore proposed that the drive for the scraper 14 configuration is constituted by an electric motor 18, whose active power is continuously measured by a measuring device 20. The electric active power of the motor 18 is determined at the known reference state of the binary ice fluid (e.g. ice-free operation or with a known ice concentration). On operating a binary ice making plant ice crystals 10 form, which lead to a rise in the electrical active power requirement. This rise can serve as a measurement signal for the ice concentration, provided that the electrical active power in ice-free operation is known. The signal is then used for determining the ice concentration from the electrical active power of the motor 18 or for controlling or regulating the power of the machine.

If the construction cycles of the cylinder 12, scraper 14 configuration and motor 18 are small and deliver reproducible results concerning the electric action of the motor 18, it may be possible not to carry out a determination in the ice-free state.

2. Method Involving Pressure Measurement

It has been found that the requisite pump pressure for delivering binary ice in a pipeline or container 12 is directly connected with the ice concentration. However, this pressure has no direct connection with the increasing pressure through expansion with increasing ice concentration.

On measuring the pressure of the binary ice following a pump 22 as shown in FIG. 2, said pressure is a measure of the ice concentration, provided that account is taken of a reference value, e.g. with ice-free operation or a known ice concentration. The same applies for the pressure difference over a distance. This pressure difference can also be related to the ice concentration.

Thus, by simply fitting two pressure sensors (not shown) in a pipeline information can be obtained on the binary ice state, which can then take place more precisely with further information on the electrical active power of the pump 22.

In the case of hydrodynamic pumps (e.g. centrifugal pumps) the delivery decreases with rising counter pressure or rising pressure difference, as occurs with ice concentration increases. The decreasing delivery results in a lower pump pressure, the rising ice concentration counteracting this drop. Therefore, the resulting pressure is subject to an interference from the delivery and ice concentration.

With positive-displacement pumps (e.g. geared pumps) the delivery remains approximately constant with rising counter pressure or rising pressure difference, as occurs when the ice concentration increases (and always much more constant than with hydrodynamic pumps). Thus, with positive-displacement pumps the pressure or pressure difference increase is even more marked. They are consequently suitable for a more precise measurement.

In a branched pipe and container system, whose flow conditions are variable (e.g. opening or closing fittings, switching processes, variable pressures/counterpressures, etc.), the pressure or pressure difference can be subject to additional changes.

Despite the aforementioned interferences and changes it is possible to isolate from secondary influences the pressure to be applied by a pump 22 or the prevailing pressure difference in a pipeline or in a container 12 to such an extent that the change in the pressure or pressure change can be used as a measure for the ice concentration. Optionally, a calibration should be carried out. Advantageously, the pressure (difference) measurement is carried out at measurement locations whose arrangement, geometry and construction are standardized, so that a factory-side measurement location definition exists. These are e.g. the entrance and/or exit from the ice making plant or a clearly defined pipe section.

As the pressure as a measure of the pump power is directly proportional to the electrical active power of the pump 22, this can also be used as a measure for the ice concentration, provided that there are standardized geometrical conditions following the pump 22.

In an alternate embodiment, a stirrer element 24 is provided along a shaft 26 of the scrapper 14 configuration within the cylindrical container 12 to assist in removing the ice crystals 10 that form along the inner surface 16 of the cylindrical container 12, as shown in FIG. 2.

Kindly delete the fifth full paragraph in the English translated specification as originally filed on page 2 starting with the text "Further advantages and features . . . " and replace it with the following text and Heading:

The invention may be best understood by those having ordinary skill in the art by reference to the following detailed description when considered in conjunction with the accompanying drawings in which:

FIG. 1 depicts the steps of the preferred method of the present invention; and FIG. 2 illustrates an apparatus used to practice the method of the present invention.

DETAILED DESCRIPTION OF THE PREFERRED EMBODIMENT

Having thus described the invention, what is claimed and desired to be secured by Letters Patent is:

1. A method for determining a changing ice concentration within a binary ice fluid volume located within a pipeline, the pipeline having an inner surface, the pipeline inner surface having ice crystals formed therealong, the steps comprising:

a) providing a means for removing the ice crystals formed along the pipeline inner surface;

b) engaging the means for removing the ice crystals such that it moves through the pipeline and removes the ice crystals from the pipeline inner surface;

c) determining on a continuing basis a fluctuating electrical power requirement of the means for removing the ice crystals as it moves through the pipeline; and d) measuring the changing ice concentration within the binary ice volume by utilizing the fluctuating electrical power requirements.

2. The method of claim 1, wherein the means for removing the ice crystals formed along the pipeline inner surface includes a rotary scraper powered by an electric motor.

3. The method of claim 2, wherein the step of determining on a continuing basis a fluctuating electrical power requirement is completed by measuring an electric potential output of the electric motor as the electric motor drives the scraper through the pipeline.

4. The method of claim 3, wherein the electrical potential output of the motor decreases as the scraper encounters concentrations of ice crystals formed g the pipeline inner surface and increases as the scraper encounters less or no concentrations of ice crystals formed along the pipeline inner surface.

5. The method of claim 1, wherein the means for removing the ice crystals formed along the pipeline inner surface further includes at least one stirrer element disposed within the pipeline.

6. The method of claim 2, wherein the electric motor includes a pump for delivering the binary ice fluid to the pipeline.

7. The method of claim 2, wherein the step of determining on a continuing basis a fluctuating electrical power requirement is completed by measuring a pressure level within the pipeline.

* * * * *